United States Patent
Chapman et al.

[11] Patent Number: 5,947,894
[45] Date of Patent: Sep. 7, 1999

[54] DISPOSABLE ENDOSCOPE SHIELD AND METHOD

[75] Inventors: David P. Chapman, Orlando, Fla.; Ronald K. Folse, Gretna, La.

[73] Assignee: Endolap, Inc., Orlando, Fla.

[21] Appl. No.: 08/976,020

[22] Filed: Nov. 21, 1997

[51] Int. Cl.$^6$ ..................... A61B 1/04
[52] U.S. Cl. ..................... 600/119; 128/857
[58] Field of Search ................ 600/114, 119; 128/849, 850, 852, 851, 853, 857; 359/510, 511, 513

[56] References Cited

U.S. PATENT DOCUMENTS

| | | |
|---|---|---|
| 3,144,020 | 8/1964 | Zingale . |
| 4,516,968 | 5/1985 | Marshall et al. . |
| 4,593,681 | 6/1986 | Soni . |
| 4,834,068 | 5/1989 | Gottesman . |
| 4,848,322 | 7/1989 | Dash et al. . |
| 4,958,623 | 9/1990 | Rocco . |
| 4,976,254 | 12/1990 | Dash et al. . |
| 5,024,212 | 6/1991 | Bonnet et al. . |
| 5,123,402 | 6/1992 | Vandenbossche et al. . |
| 5,305,765 | 4/1994 | Potts . |
| 5,388,593 | 2/1995 | Thomalla . |
| 5,522,403 | 6/1996 | Bark et al. . |

*Primary Examiner*—Beverly M. Flanagan
*Attorney, Agent, or Firm*—Allen, Dyer, Doppelt, Milbrath & Gilchrist, P.A.

[57] ABSTRACT

A disposable shield for positioning on a shaft of an endoscope to shield the user has a generally rigid, disposable shield body. The transparent plastic shield body has an opening in a medial portion thereof and a disposable elastomeric body, made from a closed cell plastic foam material, positioned in the opening. The elastomeric body has an undersized shaft opening in a medial portion thereof for contacting and securing the shaft of the endoscope therein, while permitting angular alignment of the shaft relative to the shield body. The shield body includes a convex upper portion on a protected side and a planar lower portion adjacent the convex upper portion. Ribbed edge portions provide additional stiffening to the shield body. Integrally formed sidewall portions extend outwardly from the protected side which define a generally cylindrical chamber for receiving the elastomeric body therein. An adhesive layer is provided for securing the elastomeric body to the sidewall portions and flange portions extending therefrom. Further, an elastic impermeable sealing membrane is positioned over the elastomeric body adjacent the protected side thereof. The sealing membrane has a shaft opening therein in registration with the shaft opening of the elastomeric body. A flanged cap frictionally engages with the side wall portions and secures the sealing membrane in place. The outwardly extending sidewall portions define a chamber for receiving the elastomeric body therein.

65 Claims, 2 Drawing Sheets

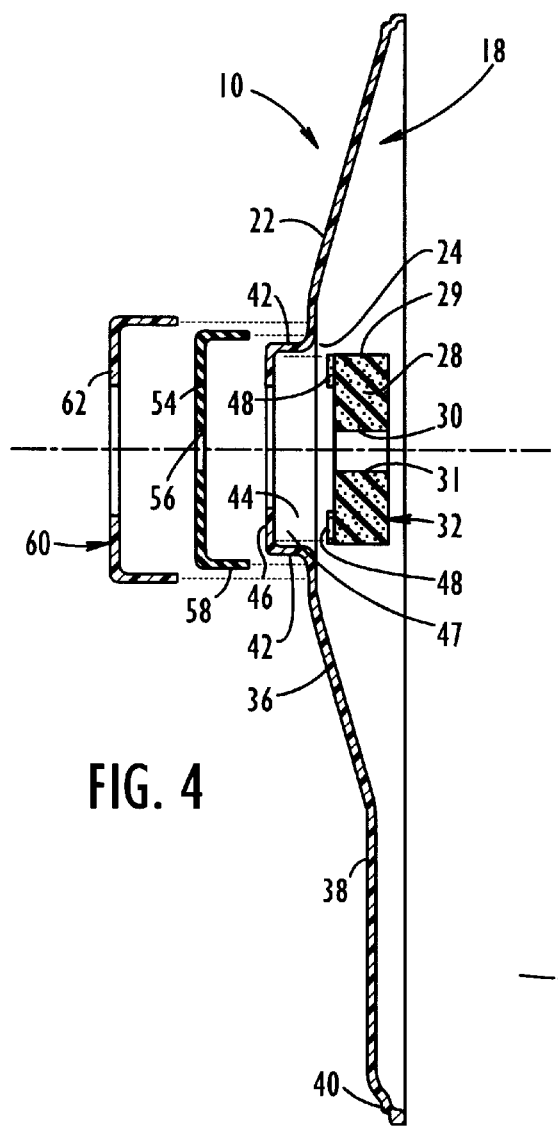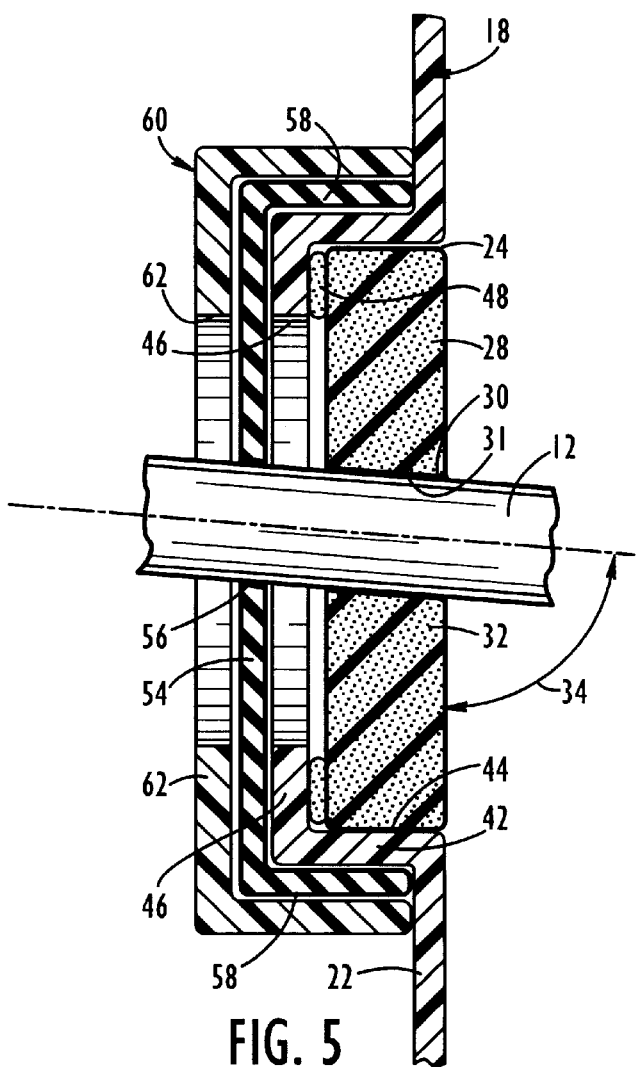

5,947,894

DISPOSABLE ENDOSCOPE SHIELD AND METHOD

FIELD OF THE INVENTION

The present invention elates to the field medical devices, and more particularly to a protective shield for endosopists.

BACKGROUND OF THE INVENTION

The present invention is directed to a disposable shield to be positioned on the shaft of an endoscope adjacent the eyepiece for protecting the endoscopic surgeon from splash (reflux) during Urologic, Gynecologic, and Ear Nose and Throat (ENT) endoscopic procedures, by way of example. Urologic procedures, known as Cystoscopy and Ureterorenosopy include examinations of the urethal tract, bladder, ureters and kidneys. Gynecologic procedure, known as Hysteroscopy, includes diagnostic examination of the cervix, vagina and surrounding anatomy. ENT includes diagotic and minimally invasive surgical procedures of the si uses and surrounding anatomy. It is with the needs created by such environments that the present invention was developed.

By way of further example, during Cystoscopy, an endoscope is passed transuretherally into the bladder for diagnosis of pathology pertaining to the urethra, prostate, bladder neck and bladder. Ureterorenoscopy pertains to operative and diagnostic procedures of the ureters an kidneys. A ureteroscope is passed transuretherally into the bladder and then inserted into the ureteral opening for visualization of the ureters and kidneys. Minimally invasive urgery may be performed during both procedures. The most common Urological surgical procedures are removal of the prostate gland and kidney stone removal from the ureters and kidneys. The prostate surgery is known as Transuretheral Resection of the Prostate (TURP). During ENT procedures, an endoscope is passed transnasally into the sinuses for view of the maxillary and frontal sinuses. Biopsy and other minimally invasive procedures may be accomplished using this technique. During Gynecologic procedures, a endoscope (hysteroscope) is passed transvaginally for viewing of the cervix, vagina and surrounding anatomy. Versatility is thus demanded for any shield that is intended to be used in such a variety of circumstances.

As recognized in the art and as addressed in U.S. Pat. 4,958,623 to Rocco, the field of view is impacted and as disclosed, a protective shield is typically arranged to encompass an eyepiece for displaying an operating field. Rocco '623 discloses a shield rigidly attached to the eyepiece, thus moving with the movement of the endoscope creating a restrictive condition.

U.S. Pat. No. 4,834,068 to Gottesman discloses an endoscope shield mounted on the shaft of an endoscope by a thin elastic annulus permitting the shaft to freely move. As a result, the shield is relatively unstable on the shaft.

U.S. Pat. Nos. 4,848,322 and 4,976,254 to Dash et al. disclose an endoscope shield including a flexible clear plastic sheet and an outer rim. The clear plastic sheet includes a flexible outer rim to permit a user to adjust its shape, and a uniform surface for avoiding distortion when viewing through the shield. The rim may include a malleable wire to retain the rim in position. A hole is provided in the shield for receiving the eyepiece of the endoscope. A plurality of radial slits extend outwardly from the hole. An annular resilient membrane is adhered to the plastic shield and extends outwardly from the radial slits. A hard rubber collar is also adhered to the shield to provide reinforcement for the opening and to help to stabilize the shield which is mounted on the endoscope. As disclosed, the radius of the stretchable collar is selected such that a small amount of stretching or expanding of collar permits a variety of sizes of endoscopes to pass through opening when the collar is adhered to a plastic sheet. The collar is spaced from the instrument shaft. The flexible outer rim portion includes a malleable wire embedded in the plastic shield for retaining the shield in a desired shape. It would serve the art well to provide a simpler structure that is less expensive to construct and thus lends itself to be less costly to construct and appropriate for one time use and disposable.

U.S. Pat. No. 4,593,681 to Soni discloses a device for stabilizing the sheath of an endoscope or arthroscope during surgery. The device is a relatively thin, flat, flexible plate of plastic having a bow or figure-eight shape and which is placed against a patient's body at the area of penetration. A rotatable cam mechanism secures the plate to the shaft of the scope. An annularly shaped soft flexible bushing having a central opening is clamped against the top annular surface of a stud by an internally threaded plastic end cap. Rotation of the end car compresses the bushing. The disclosure provides that the embodiments are not disposable and are intended for reuse in various arthroscopic surgery procedures after sterilizing the same between procedures. The present invention seeks to satisfy a need for a simply constructed, low cost, and disposable shield.

SUMMARY OF THE INVENTION

In view of the foregoing background, it is therefore an object of the present invention to provide a disposable shield for protecting clinicians and medical staff from inadvertent contact with potentially infectious body fluids during various endoscopic procedures, and the like, while enhancing ease in handling required instruments. For ease in reading and by way of example only, the present invention will be described with an endoscopic as a work piece, by way of example. However, it will be clear that other uses, such as earlier described in the background section of this specification, will receive benefit from the present invention. It is further an object of the present invention to provide for simple manufacturer and low cost for such a shield.

These and other objects, advantages and features of the present invention are provided by a disposable endoscope shield for positioning on a shaft of an endoscope to shield the user. The disposable endoscope shield preferably comprises a disposable shield body being generally rigid and defining a working side adjacent a patient and a protected side opposite the working side. The shield body has an opening in a medial portion thereof. A disposable elastomeric body is positioned in the opening, the elastomeric body having an undersized shaft opening in a medial portion thereof for contacting and securing the shaft of the endoscope therein and while permitting angular alignment of the shaft relative to the shield body.

In one preferred embodiment, the shield body further comprises a convex upper portion on the protected side and a planar lower portion adjacent the convex upper portion. Ribbed edge portions provide additional stiffening to the shield body. The shield body comprises a transparent plastic material.

A disposable endoscope shield is provided wherein the shield body further comprises integrally formed sidewall portions extending outwardly from the protected side and defining a chamber receiving the elastomeric body therein. Integrally formed flange portions extend radially inwardly from ends of the sidewall portions. An adhesive layer is provided for securing the elastomeric body to at least one of the sidewall portions and the flange portions.

In a preferred embodiment, the elastomeric body has a generally cylindrical shape. At least one slit extends radially inwardly to the shaft opening. The elastomeric body comprises an closed cell plastic foam material. The elastomeric body has a generally cylindrical shape with an outer diameter in a range of about 3 to 8 times a diameter of the shaft opening.

A sealing membrane is positioned over the elastomeric body adjacent the protected side thereof. The sealing membrane has a shaft opening therein in registration with the shaft opening of the elastomeric body. The sealing membrane comprises an elastic impermeable material for sealing against the endoscope shaft. The shield body comprises integrally formed sidewall portions extending outwardly from the protected side and defining a chamber receiving the elastomeric body therein. The sealing membrane includes edge portions extending over the sidewall portions, and further comprises an end cap positioned over the edge portions of the sealing membrane for securing same to adjacent sidewall portions. The end cap slides onto and frictionally engages with adjacent sidewall portions of the shield body. In yet another embodiment, flange portions extend radially inwardly from ends of the sidewall portions and the end cap further comprises radially inwardly extending flange portions coextensive with the flange portions of the shield body. Radially innermost edges of the flanges of the sidewall portions and flanges of the end cap are spaced from the shaft opening of the elastomeric body a predetermined distance. In one embodiment, the predetermined distance is in a range of about 1 to 5 times a diameter of the shaft opening.

A method aspect of the present invention is for making a disposable endoscope shield for positioning on a shaft of an endoscope to shield a user. The method comprises the steps of providing a disposable shield body being generally rigid and defining a working side adjacent a patient and a protected side opposite the working side, said shield body having an opening in a medial portion thereof, and positioning a disposable elastomeric body positioned in said opening, said elastomeric body having an undersized shaft opening in a medial portion thereof for contacting and securing the shaft of the endoscope therein and while permitting angular alignment of the shaft relative to the shield body. Further, the shield is formed with a convex upper portion on the protected side and a planar lower portion adjacent said convex upper portion. Ribbed portions are formed in said shield body for providing additional stiffening to said shield body. In one preferred embodiment, as earlier described, the shield comprises a transparent plastic material.

Sidewall portions are integrally formed which extend outwardly from the protected side and define a chamber from the sidewall portion for receiving said elastomeric body within the chamber. Flange portions are integrally formed and extend radially inwardly from ends of the sidewall portions. An adhesive layer is applied for securing said elastomeric body to at least one of said sidewall portions and said flange portions. A sealing membrane is positioned over said elastomeric body adjacent the protected side thereof, said sealing membrane having a shaft opening therein in registration with the shaft opening of said elastomeric body.

BRIEF DESCRIPTION OF THE DRAWINGS

A preferred embodiment as well as alternate embodiments of the invention are described, by way of example, with reference to the accompanying drawings in which:

FIG. 4 is a partial exploded cross-sectional view taken through lines 4—4 of FIG. 1; and FIG. 5 is a partial cross-sectional view taken through lines 5—5 of FIG. 1.

DETAILED DESCRIPTION OF THE PREFERRED EMBODIMENTS

The present invention will now be described more fully hereinafter with reference to the accompanying drawings, in which a preferred embodiment of the invention is shown. This invention may, however, be embodied in many different forms and should not be construed as limited to any one embodiment set forth herein. Rather, the embodiment is provided so that this disclosure will be thorough and complete, and will fully convey the scope of the invention to those skilled in the art. Like numbers refer to like elements throughout.

Figure 1:
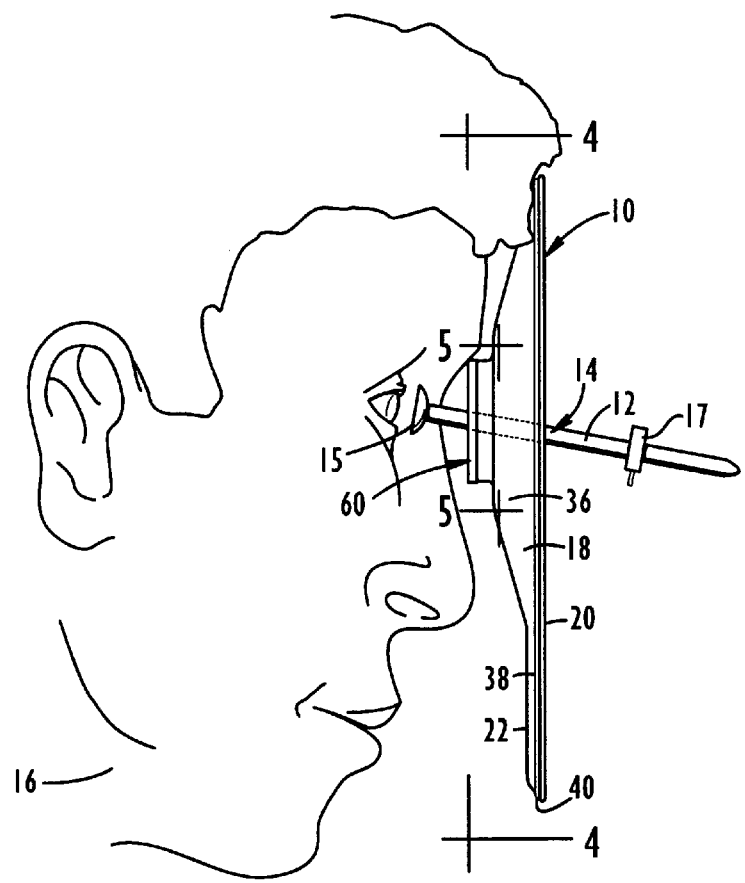
FIG. 1 is a perspective view of an embodiment of the present invention positioned with a user.
Figure 2:
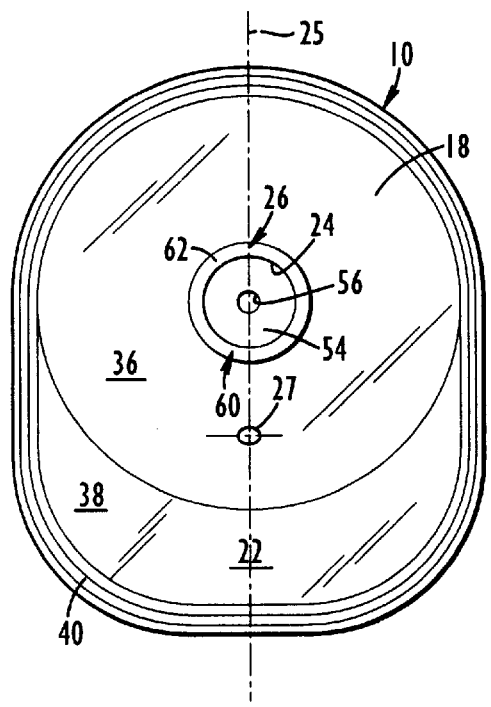
FIG. 2 is a plan view of a protected side of the embodiment of FIG. 1.
Figure 3:
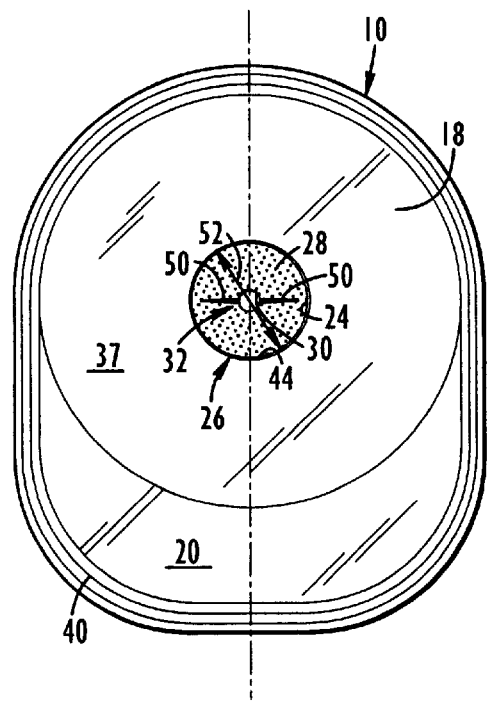
FIG. 3 is a plan view of a working side of the embodiment of FIG. 1.

Referring now to FIGS. 1–5, a disposable endoscope shield 10 for positioning on a hub or shaft 12 of an endoscope 14, described herein by way of example, to shield the user 16 comprises a disposable shield body 18. The shield 10 is generally positioned between an eyepiece 15 and a light post 17, as illustrated with reference again to FIG. 1, by way of example. The shield body 18 is generally rigid and defines a working side 20 adjacent a patient and a protected side 22 opposite the working side and adjacent the user 16. The shield body 18 has an opening 24 in a medial portion 26 thereof. As illustrated with reference to FIGS. 3–5, an elastomeric body 28 is positioned in the opening 24. The elastomeric body 28 has an undersized shaft opening 30 in a medial portion 32 thereof for contacting and securing the shaft 12 of the endoscope 14 therein and while permitting some angular alignment 34 of the shaft relative to the shield body 18. Further, a thickness 29 of the elastomeric body 28 is selected relative to the opening 30 for permitting sufficient frictional contact between the shaft 12 and elastomeric body bore walls 31 for generally holding the alignment 34. As a result, the shield 10 is held in place without slipping, turning, wobbling or otherwise moving from its desired position set by the user 16.

In one preferred embodiment, and as illustrated again with reference to FIGS. 1–4, the shield body 18 further comprises a convex upper portion 36 on the protected side 22 and a planar lower portion 38 adjacent the convex upper portion. Such a contour permits the user 16 to get his nose and face portions get close to the shield 10 thus enhancing the shielding to the user. As will be appreciated for the embodiment herein described by way of example, a concave upper portion 37 opposes the convex upper portion 36 when a sheet material is used for the shield body 18. Ribbed edge portions 40 provide additional stiffening to the shield body 18. In a preferred embodiment, the shield body comprises a transparent plastic material.

As illustrated with particular reference again to FIGS. 4 and 5, the disposable endoscope shield 10 is provided wherein the shield body 18 further comprises integrally formed sidewall portions 42 extending outwardly from the protected side 22 and defining a chamber 44 receiving the elastomeric body 28 therein. Integrally formed flange portions 46 extend radially inwardly from ends of the sidewall portions 42. In one preferred embodiment, an adhesive layer 48 is provided for securing the elastomeric body 28 to at least one of the sidewall portions 42 and the flange portions. As illustrated again with reference to FIGS. 4 and 5, the adhesive layer 48 is applied for attachment to a working side surface 47 of the flange portion 46. Alternate embodiments include ultrasonic welding as a bonding means between the elastomeric body 28 and shield body 18 as will be appreciated by those of ordinary skill in the art.

In a preferred embodiment, the elastomeric body 28 has a generally cylindrical shape. As illustrated with reference again to FIG. 3, two slits 50 extends radially inwardly to the elastomeric body shaft opening 30. Such slits 50, as illustrated with reference to FIG. 3, permit ease in passing the eyepiece 15 of the endoscope 14 through the opening 30 without compromising a snug fit around the shaft 12 as it extends through the opening 30. As earlier described, the snug fit permits the shaft 12 to be held with the shield 10 without a "floppy" or free movement of the shield about the shaft. Such permits the user 16 to manipulate the shield 10 through movement of the endoscope 14. It has been found that a closed cell plastic foam material provides an effective elastomeric body 28. Such prevents migration of fluids along the shaft 12, thereby maintaining sterility on the protected side 22 and thus to the user 16. Often, the user 16 is looking upward, and often a victim of gravity. Further, and as illustrated with reference again to FIGS. 3–5, the elastomeric body 28 has a generally cylindrical shape with an outer diameter, illustrated with reference again to FIG. 3, in a range of about 3 to 8 times a diameter of the body shaft opening 30. The body shaft opening 30 is approximately equal to the thickness 29 of the elastomeric body 28.

As illustrated again with reference to FIG. 2. The opening 24, is offset along a longitudinal axis 25 with respect to a geometric center 27 of the shield 10. Such asymmetry permits the shield 10 to be rotated about the endoscope shaft 12 for selectively shielding portions of the user 16. This in combination with the endoscope 14 being frictionally held in position about the shaft 12 frees up a hand of the user 16.

As illustrated with reference again to FIGS. 2, 4 and 5, a sealing membrane 54 is positioned over the elastomeric body 28 adjacent the protected side 22 thereof. The sealing membrane 54 has a shaft opening 56 therein in registration with the body shaft opening 30 of the elastomeric body 28. The sealing membrane 54 comprises an elastic impermeable material for further sealing against the endoscope shaft 12.

As earlier described, and as illustrated with reference again to FIGS. 4 and 5, the shield body 18 comprises the sidewall portions 42 integrally formed and extending outwardly from the protected side and defining the chamber 44 receiving the elastomeric body 28 therein. In a preferred embodiment, the sealing membrane 54 includes edge portions 58 extending over the sidewall portions 42, and further comprises an end cap 60 positioned over the edge portions 58 of the sealing membrane 54 for securing same to adjacent sidewall portions 42. The end cap 60, for a preferred embodiment, slides onto and frictionally engages with adjacent sidewall portions 42 of the shield body 18. As herein described, the flange portions 46 extend radially inwardly from ends of the sidewall portions 42. The end cap 60 in a preferred embodiment, further comprises radially inwardly extending flange portions 62 coextensive with the flange portions 46 of the shield body 18. Radially innermost edges 64, 66 of the flange portions 46, 62 are spaced from the shaft opening 30 of the elastomeric body 28 a predetermined distance. In one embodiment, the predetermined distance is in a range of about 1 to 5 times a diameter of the shaft opening 30.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed or suggested, and that modifications and embodiments are intended to be included within the scope of the appended claims.

That which is claimed is:

1. A disposable endoscope shield for positioning on a shaft of an endoscope to shield the user, said disposable endoscope shield comprising:

a disposable shield body being generally rigid and defining a working side adjacent a patient and a protected side opposite the working side, said shield body having an opening in a medial portion thereof, said body further having a convex upper portion on the protected side and a planar lower portion adjacent said convex upper portion; and a disposable elastomeric body positioned in said opening, said elastomeric body having an undersized opening in a medial portion thereof for contacting and securing the shaft of the endoscope therein and while permitting angular alignment of the shaft relative to the shield body.

2. A disposable endoscope shield according to claim 1, wherein said shield body further comprises ribbed edge portions for providing additional stiffening to said shield body.

3. A disposable endoscope shield according to claim 1, wherein said shield body comprises a transparent material.

4. A disposable endoscope shield according to claim 1, wherein said shield body comprises a plastic material.

5. A disposable endoscope shield according to claim 1, wherein said shield body further comprises integrally formed sidewall portions extending outwardly from the protected side and defining a chamber receiving said elastomeric body therein.

6. A disposable endoscope shield according to claim 5, further comprising integrally formed flange portions extending radially inwardly from ends of the sidewall portions.

7. A disposable endoscope shield according to claim 6, further comprising a bond between said elastomeric body and at least one of said sidewall portions and said flange portions.

8. A disposable endoscope shield according to claim 1, wherein said elastomeric body has a generally cylindrical shape.

9. A disposable endoscope shield according to claim 1, wherein said elastomeric body has at least one slit extending radially inwardly to the shaft opening.

10. A disposable endoscope shield according to claim 1, wherein said elastomeric body comprises an closed cell plastic foam material.

11. A disposable endoscope shield according to claim 1, wherein said elastomeric body has a generally cylindrical shape with an outer diameter in a range of about 3 to 8 times a diameter of the opening and a width proximate the diameter of the opening.

12. A disposable endoscope shield for positioning on a shaft of an endoscope to shield the user, said disposable shield comprising:

a disposable shield body being generally rigid and defining a working side adjacent a patient and a protected side opposite the working side, said shield body having an opening in a medial portion thereof;

a disposable elastomeric body positioned in said opening, said elastomeric body having an undersized opening in a medial portion thereof for contacting and securing the shaft of the endoscope therein and while permitting angular alignment of the shaft relative to the shield body; and a sealing membrane positioned over said elastomeric body adjacent the protected side thereof, said sealing membrane having a shaft opening therein in registration with the shaft opening of said elastomeric body.

13. A disposable endoscope shield according to claim 12, wherein said sealing membrane comprises an elastic impermeable material for sealing against the endoscope shaft.

14. A disposable endoscope shield according to claim 12, wherein said shield body further comprises integrally formed sidewall portions extending outwardly from the protected side and defining a chamber receiving said elastomeric body therein; wherein said sealing membrane includes edge portions extending over said sidewall portions; and further comprising an end cap positioned over the edge portions of said sealing membrane for securing same to adjacent sidewall portions.

15. A disposable endoscope shield according to claim 14, wherein said end cap slides onto and frictionally engages with adjacent sidewall portions of said shield body.

16. A disposable endoscope shield according to claim 14, further comprising flange portions extending radially inwardly from ends of the sidewall portions; and wherein said end cap further comprises radially inwardly extending flange portions coextensive with the flange portions of said shield body.

17. A disposable endoscope shield according to claim 16, wherein radially innermost edges of the flanges of said sidewall portions and flanges of said end cap are spaced from the shaft opening of said elastomeric body a predetermined distance.

18. A disposable endoscope shield according to claim 17, wherein said predetermined distance is in a range of about 1 to 5 times a diameter of the shaft opening.

19. A disposable endoscope shield according to claim 1, wherein said opening is positioned along a longitudinal axis of said shield body and offset from a center point thereof.

20. A method for making a disposable endoscope shield for positioning on a shaft of an endoscope to shield a user, the method comprising the steps of:

providing a disposable shield body being generally rigid and defining a working side adjacent a patient and a protected side opposite the working side, said shield body having an opening in a medial portion thereof;

forming a convex upper portion on the protected side;

forming a planar lower portion adjacent said convex upper portion; and positioning a disposable elastomeric body positioned in said opening, said elastomeric body having an undersized shaft opening in a medial portion thereof for contacting and securing the shaft of the endoscope therein and while permitting angular alignment of the shaft relative to the shield body.

21. A method according to claim 20, further comprising the step of forming ribbed edge portions in said shield body for providing additional stiffening to said shield body.

22. A method according to claim 20, wherein said shield body comprises a transparent material.

23. A method according to claim 20, wherein said shield body comprises a plastic material.

24. A method according to claim 20, further comprising the steps of:

integrally forming sidewall portions extending outwardly from the protected side;

defining a chamber from the sidewall portion; and receiving said elastomeric body within the chamber.

25. A method according to claim 24, further comprising the step of integrally forming flange portions extending radially inwardly from ends of the sidewall portions.

26. A method according to claim 25, further comprising the step of applying an adhesive layer for bonding and securing said elastomeric body to at least one of said sidewall portions and said flange portions.

27. A method according to claim 20, wherein said elastomeric body has a generally cylindrical shape.

28. A method according to claim 20, wherein said elastomeric body has at least one slit extending radially inwardly to the shaft opening.

29. A method according to claim 20, wherein said elastomeric body comprises an closed cell plastic foam material.

30. A method according to claim 20, wherein said elastomeric body has a generally cylindrical shape with an outer diameter in a range of about 3 to 8 times a diameter of the shaft opening.

31. A method for making a disposable endoscope shield for positioning on a shaft of an endoscope to shield a user, the method comprising the steps of:

providing a disposable shield body being generally rigid and defining a working side adjacent a patient and a protected side opposite the working side, said shield body having an opening in a medial portion thereof;

positioning a disposable elastomeric body positioned in said opening, said elastomeric body having an undersized shaft opening in a medial portion thereof for contacting and securing the shaft of the endoscope therein and while permitting angular alignment of the shaft relative to the shield body, and positioning a sealing membrane over said elastomeric body adjacent the protected side thereof, said sealing membrane having a shaft opening therein in registration with the shaft opening of said elastomeric body.

32. A method according to claim 31, wherein said sealing membrane comprises an elastic impermeable material for sealing against the endoscope shaft.

33. A method according to claim 31, further comprising the steps of:

integrally forming sidewall portions extending outwardly from the protected side;

defining a chamber receiving said elastomeric body therein, wherein said sealing membrane includes edge portions extending over said sidewall portions;

positioning an end cap over the edge portions of said sealing membrane; and securing said sealing membrane to adjacent sidewall portions.

34. A method according to claim 33, wherein said end cap slides onto and frictionally engages with adjacent sidewall portions of said shield body.

35. A method according to claim 33, further comprising the steps of:

providing flange portions extending radially inwardly from ends of the sidewall portions; and providing radially inwardly extending flange portions to said end cap;

coextensively placing flanges of said end cap with the flange portions of said shield body.

36. A method according to claim 35, wherein radially innermost edges of the flanges of said sidewall portions and flanges of said end cap are spaced from the shaft opening of said elastomeric body a predetermined distance.

37. A method according to claim 36, wherein said predetermined distance is in a range of about 1 to 5 times a diameter of the shaft opening.

38. A disposable endoscope shield for positioning on a shaft of an endoscope to shield the user, said disposable endoscope shield comprising:

a disposable shield body being generally rigid and defining a working side adjacent a patient and a protected side opposite the working side, said shield body having an opening in a medial portion thereof and ribbed edge portions formed within said shield body for providing additional stiffening thereto; and a disposable elastomeric body positioned in said opening, said elastomeric body having an undersized opening in a medial portion thereof for contacting and securing the shaft of the endoscope therein and while permitting angular alignment of the shaft relative to the shield body.

39. A disposable endoscope shield according to claim 38, wherein said shield body further comprises:

a convex upper portion on the protected side; and a planar lower portion adjacent said convex upper portion.

40. A disposable endoscope shield according to claim 38, wherein said shield body comprises a transparent material.

41. A disposable endoscope shield according to claim 38, wherein said shield body comprises a plastic material.

42. A disposable endoscope shield according to claim 38, wherein said shield body further comprises integrally formed sidewall portions extending outwardly from the protected side and defining a chamber receiving said elastomeric body therein.

43. A disposable endoscope shield according to claim 38, wherein said elastomeric body has a generally cylindrical shape.

44. A disposable endoscope shield according to claim 38, wherein said elastomeric body comprises an closed cell plastic foam material.

45. A disposable endoscope shield according to claim 38, wherein said elastomeric body has a generally cylindrical shape with an outer diameter in a range of about 3 to 8 times a diameter of the opening and a width proximate the diameter of the opening.

46. A disposable endoscope shield according to claim 38, further comprising a sealing membrane positioned over said elastomeric body adjacent the protected side thereof, said sealing membrane having a shaft opening therein in registration with the shaft opening of said elastomeric body.

47. A disposable endoscope shield according to claim 38, wherein said opening is positioned along a longitudinal axis of said shield body and offset from a center point thereof.

48. A disposable endoscope shield for positioning on a shaft of an endoscope to shield the user, said disposable endoscope shield comprising:

a disposable shield body being generally rigid and defining a working side adjacent a patient and a protected side opposite the working side, said shield body having an opening in a medial portion of said shield body, wherein said opening is positioned along a longitudinal axis of said shield body and offset from a center point thereof; and a disposable elastomeric body positioned in said opening, said elastomeric body having an undersized opening in a medial portion thereof for contacting and securing the shaft of the endoscope therein and while permitting angular alignment of the shaft relative to the shield body.

49. A disposable endoscope shield according to claim 48, wherein said shield body further comprises:

a convex upper portion on the protected side; and a planar lower portion adjacent said convex upper portion.

50. A disposable endoscope shield according to claim 48, wherein said shield body further comprises ribbed edge portions for providing additional stiffening to said shield body.

51. A disposable endoscope shield according to claim 48, wherein said shield body comprises a transparent material.

52. A disposable endoscope shield according to claim 48, wherein said shield body comprises a plastic material.

53. A disposable endoscope shield according to claim 48, wherein said shield body further comprises integrally formed sidewall portions extending outwardly from the protected side and defining a chamber receiving said elastomeric body therein.

54. A disposable endoscope shield according to claim 48, wherein said elastomeric body has a generally cylindrical shape.

55. A disposable endoscope shield according to claim 48, wherein said elastomeric body comprises an closed cell plastic foam material.

56. A disposable endoscope shield according to claim 48, wherein said elastomeric body has a generally cylindrical shape with an outer diameter in a range of about 3 to 8 times a diameter of the opening and a width proximate the diameter of the opening.

57. A disposable endoscope shield according to claim 48, further comprising a sealing membrane positioned over said elastomeric body adjacent the protected side thereof, said sealing membrane having a shaft opening therein in registration with the shaft opening of said elastomeric body.

58. A method for making a disposable endoscope shield for positioning on a shaft of an endoscope to shield a user, the method comprising the steps of:

providing a disposable shield body being generally rigid and defining a working side adjacent a patient and a protected side opposite the working side, said shield body having an opening in a medial portion thereof;

forming ribbed edge portions in said shield body for providing additional stiffening to said shield body; and positioning a disposable elastomeric body positioned in said opening, said elastomeric body having an undersized shaft opening in a medial portion thereof for contacting and securing the shaft of the endoscope therein and while permitting angular alignment of the shaft relative to the shield body.

59. A method according to claim 58, further comprising the steps of:

forming a convex upper portion on the protected side; and forming a planar lower portion adjacent said convex upper portion.

60. A method according to claim 58, further comprising the steps of:

integrally forming sidewall portions extending outwardly from the protected side;

defining a chamber from the sidewall portion; and receiving said elastomeric body within the chamber.

61. A method according to claim 58, further comprising the step of integrally forming flange portions extending radially inwardly from ends of the sidewall portions.

62. A method according to claim 61, further comprising the step of applying an adhesive layer for bonding and securing said elastomeric body to at least one of said sidewall portions and said flange portions.

63. A method according to claim 58, further comprising the step of forming at least one slit in the elastomeric body, said slit extending radially inwardly to the shaft opening.

64. A method according to claim 58, further comprising the step of positioning a sealing membrane over said elastomeric body adjacent the protected side thereof, said sealing membrane having a shaft opening therein in registration with the shaft opening of said elastomeric body.

65. A method according to claim 58, further comprising the steps of:

integrally forming sidewall portions extending outwardly from the protected side;

defining a chamber receiving said elastomeric body therein, wherein said sealing membrane includes edge portions extending over said sidewall portions;

positioning an end cap over the edge portions of said sealing membrane; and securing said sealing membrane to adjacent sidewall portions.

\* \* \* \* \*